United States Patent [19]
Wichman

[11] 4,143,653
[45] Mar. 13, 1979

[54] SPLINTING OF MEMBERS

[76] Inventor: Heins Wichman, 369 W. Blackwell St., Dover, N.J. 07801

[21] Appl. No.: 779,506

[22] Filed: Mar. 21, 1977

[51] Int. Cl.² ............................................. A61F 5/04
[52] U.S. Cl. ............................ 128/87 A; 128/89 R
[58] Field of Search ............... 128/87 R, 87 A, 77, 128/89 R

[56] References Cited

U.S. PATENT DOCUMENTS

| 471,252 | 3/1892 | Hanley | 128/87 R |
| 2,528,456 | 10/1950 | Stevenson | 128/87 A |
| 2,573,715 | 11/1951 | Kelly | 128/89 R |

FOREIGN PATENT DOCUMENTS

| 1286288 | 1/1962 | France | 128/89 R |
| 2599 | 3/1891 | United Kingdom | 128/89 R |
| 929317 | 6/1963 | United Kingdom | 128/87 A |

*Primary Examiner*—John D. Yasko
*Attorney, Agent, or Firm*—George E. Kersey

[57] ABSTRACT

Splinting of members, particularly injured or broken fingers, using a flexible strip with individual, perpendicular projections along one edge. The strip can be bent into a desired non-planar shape with the edge projections providing lateral support without disturbing the bendability of the strip.

2 Claims, 6 Drawing Figures

U.S. Patent   Mar. 13, 1979   Sheet 1 of 2   4,143,653
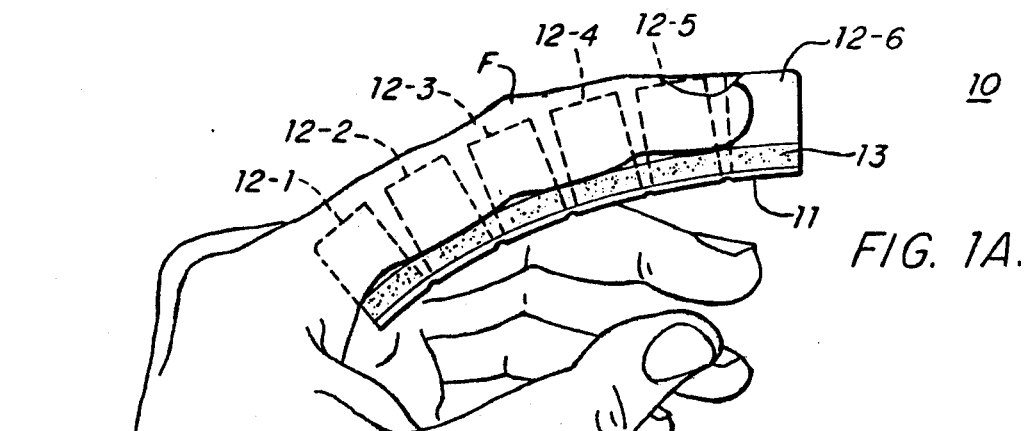
FIG. 1A.
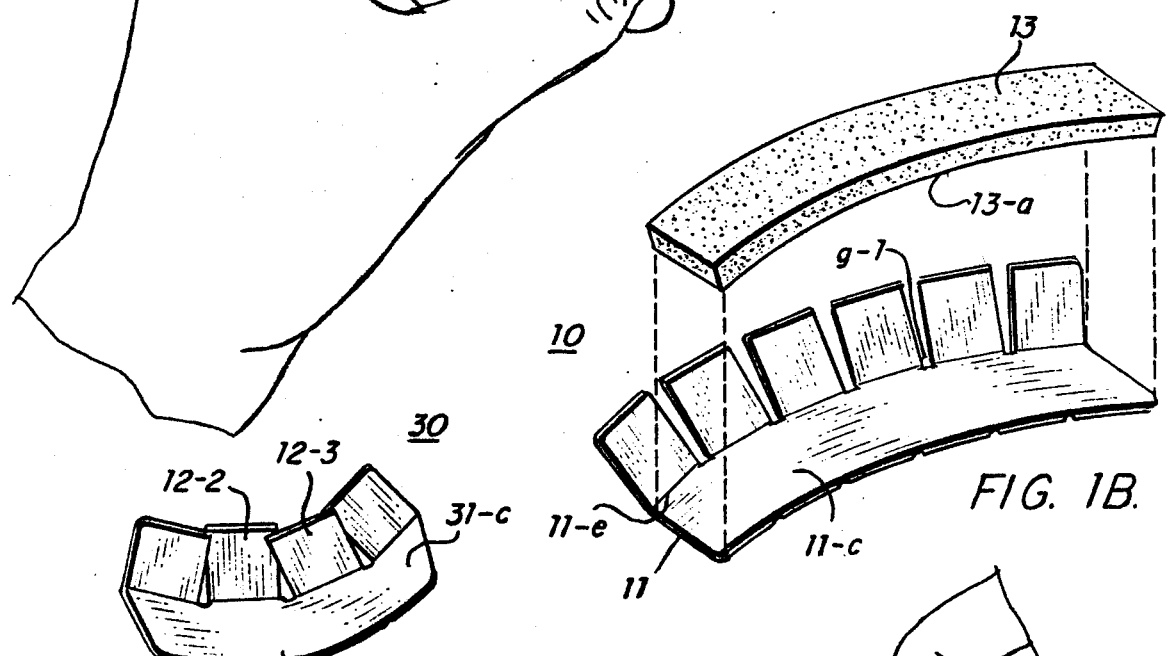
FIG. 1B.
FIG. 3.
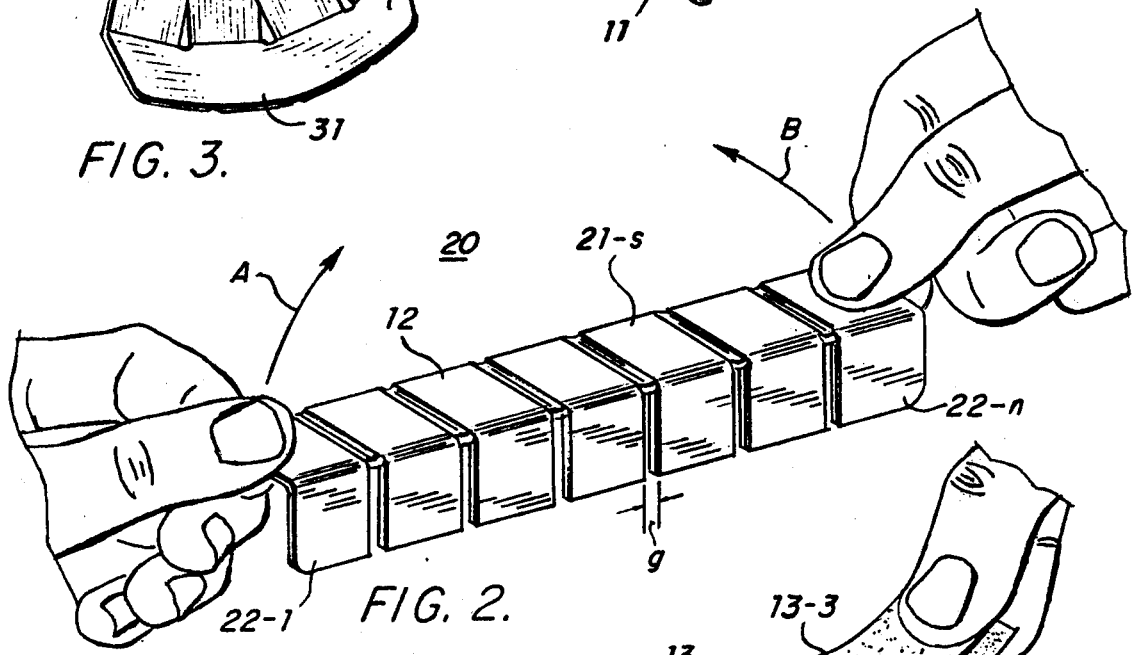
FIG. 2.
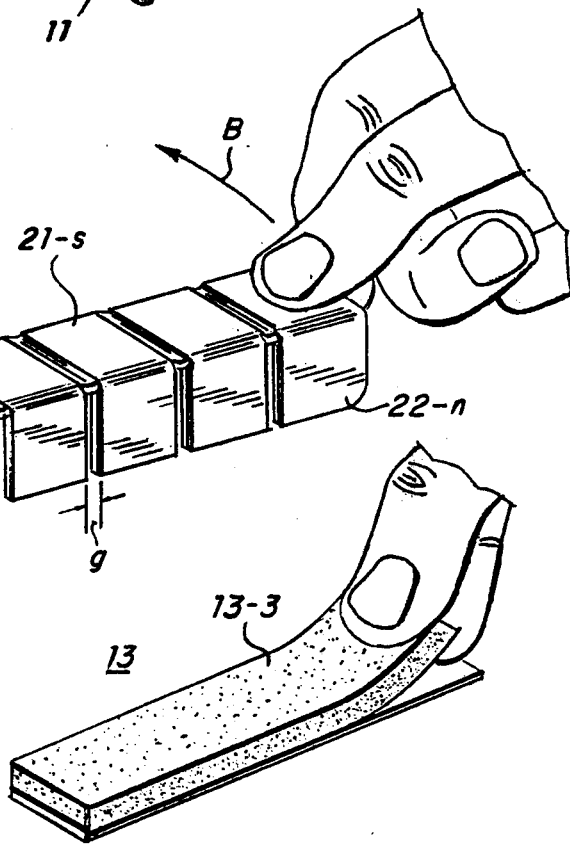
FIG. 4.

SPLINTING OF MEMBERS

BACKGROUND OF THE INVENTION

This invention relates to the splinting of members, and, more particularly, to the splinting of injured or broken fingers.

Splints are used to restrict injured and broken members, such as fingers, to a particular position until satisfactory healing has taken place. In some cases the members should be maintained in a particular bent condition. In any case, inadvertent lateral motion of the member is to be avoided since it interferes with the desired healing.

In commonly employed splinting it is extremely difficult to maintain the desired lateral immobility. The consequence is that healing is prolonged, or does not take place correctly. Where conventional splinting is inadequate it may be necessary to completely immobilize the patient. This is particularly unsatisfactory when the broken or injured part is a finger and immobilization limits the ability of the patient to perform other functions.

Accordingly, it is an object of the invention to achieve splinting which provides the desired degree of lateral support, particularly for fingers.

Another object of the invention is to provide splinting which is able to maintain a broken or injured member in a prescribed bent position. A related object is to achieve splinting in which a desired bend of an injured or broken member can be maintained until suitable healing has taken place.

A further object of the invention is to provide splinting which can be adjusted to a wide variety of bend positions, depending upon what is required for an injured or broken member.

Still another object of the invention is to achieve a universal splint which provides lateral security and can be adjusted to any desired configuration and length.

A still further object of the invention is to reduce the bulkiness of splinting for the maintenance of lateral and vertical security, particularly for broken members such as fingers.

SUMMARY OF THE INVENTION

In accomplishing the foregoing and related objects, the invention provides for the splinting of members using a flexible strip which can be bent into a desired non-planar configuration. In accordance with one aspect of the invention the flexible strip includes a series of individual, angular projections along one edge to provide lateral support without interfering with the bending operation.

In accordance with another aspect of the invention, the strip can be formed into any desired length, by breaking off one or more ends of the strip to a prescribed length. In accordance with a related aspect of the invention, the strip includes a set of grooves which facilitate the bending of the strip as well as the breakage of excess length.

In accordance with still another aspect of the invention, the strip is provided with foam padding to cushion the member that is splinted by the strip and its edge projections.

In accordance with yet another aspect of the invention, the strip can be bent into either a convex or a concave configuration.

According to a further aspect of the invention, the projections are equal tabs that extend at a right angle to the surface of the strip. To prevent the tabs from interfering with the bending, each is separated from an adjoining tab by a gap that extends into the material of the strip. This prevents ridges at the gaps from interfering with the desired bending.

DESCRIPTION OF THE DRAWINGS

Other aspects of the invention will become apparent after considering several illustrative embodiments of the invention taken in conjunction with the drawings in which:

FIG. 1A is a perspective view of a splint being used in accordance with the invention to provide lateral and vertical support to a broken of injured finger;

FIG. 1B is a perspective view of the splint of FIG. 1A with its suchion portion exploded away;

FIG. 2 is a perspective view of a splint strip in accordance with the invention being proportioned to a prescribed length;

FIG. 3 is a perspective view of an alternative configuration of a splint in accordance with the invention;

FIG. 4 is a perspective view of a cushion pad being prepared for use with a splint in accordance with the invention.

DETAILED DESCRIPTION

Figure 5:
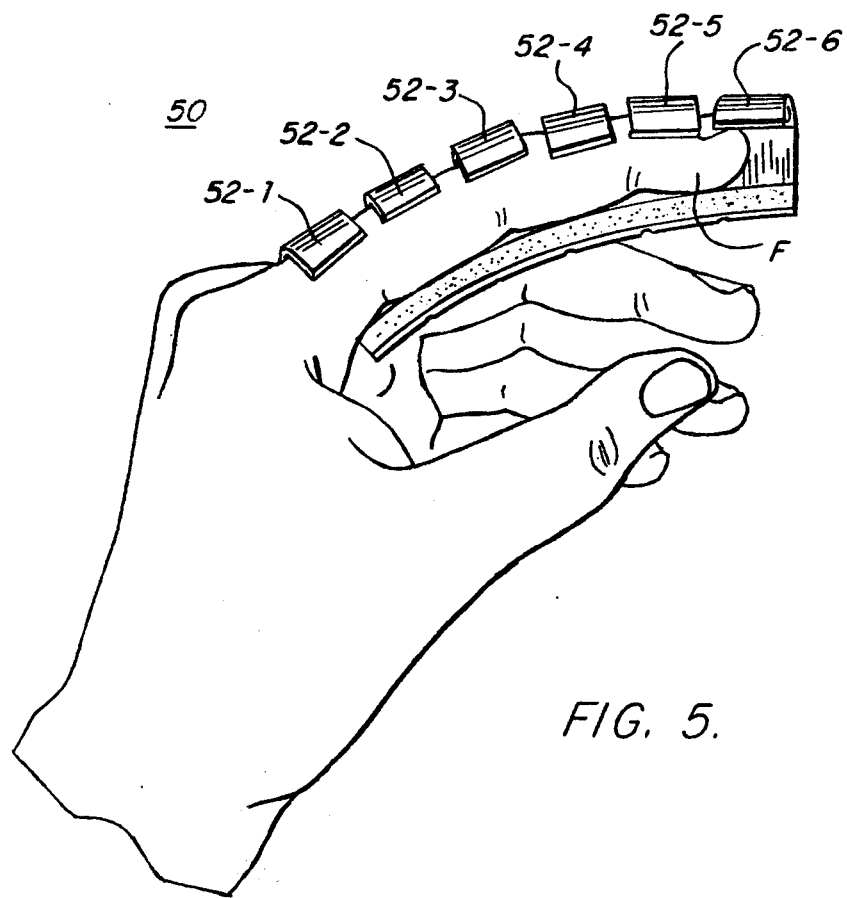
FIG. 5 is an alternate embodiment of the invention being used in the secure splinting of a finger.

Turning to the drawings, FIG. 1A shows a splint 10 which is being used to provide lateral and vertical support to an injured index finger F. The splint 10 is formed from a base strip 11 which is bent into a desired curvature according to the bend required for proper healing of the finger F. Extending upwardly from the far edge of strip 11 at a right angle are individual projections 12-1 through 12-6. The finger F is cushioned on the strip 11 by a pad 13.

Details of the splint 10 are shown in FIG. 1B. The strip 11 is bent to form a convex surface 11-c. At one edge 11-e are projections 12-1 through 12-6 which are general perpendicular to the surface 11-c. Each projection is separated at its base from an adjoining projection by a gap g-1. To permit the strip 11 to be bent into a desired configuration without interference between projections, each gap g-1 extends into the surface 11-c so that there is no material between adjoining projections at the surface 11-c. Because of the convex bend of the surface 11-c, the projections diverge from the surface so that the gaps at the tips are wider than at the bases.

As indicated by FIG. 1B, the pad 13 that is used to cushion the finger F is applied to the convex surface 11-c. The pad 13 is desirably of foam or sponge rubber with an adhesive layer 13-a that engages the convex surface 11-c.

A splint extension 20 in accordance with the invention is shown in FIG. 2. The extension 20 can easily be severed to form a strip 11 of desired size by the use of the grooves or notches 21 in the outer strip surface 21-s. As can be seen in FIG. 2, the projections 22-1 through 22-n are separated from one another by a gap g which is of uniform width from one projection to the adjoining projection, when the strip 21 is in its unbent form. To facilitate the bending, no side metal is left between projections. Thus gap g extends through the surface 21-s of the strip 21 as well as between the adjoining projections. In some cases it may be desirable to provide further relief of material between adjoining projections by the use of an indentation at each such position in the strip 21.

As indicated, the strip 21 is gripped for a desired length and bent a number of times in the direction indicated by the arrows A and B to effect a separation of the excess material from the part that is desired.

FIG. 3 illustrates a splint 30 that has been proportioned to a desired length can be bent readily to assure a concave surface 31-c for engagement with a member. In the case of FIG. 3, the gap g between adjoining projections, e.g., 12-2 and 12-3, is wider at the bases than at the tips. In fact, depending upon the extent of bending there is no gap at the tips of the projections which overlap as shown in FIG. 3.

FIG. 4 shows a type of pad 13 that is used in conjunction with the strip to provide a desired cushioning effect. Since it is advantageous for the pad 13 to adhere to the bent surface of the strips 11 and 31, the pad includes a removable release sheet 13-3 which is peeled from the pad when the latter is to be positioned on the strip. It will be apparent that the length of the pad 13 depends upon the length of the strip, as well as upon the extent of the desired cushioning. In some situations it is desirable for the pad to extend beyond the edges of the strip to provide additional cushioning.

In the embodiment of FIG. 5, the splint 50 has elongated projections 52-1 through 52-6 which are bent over the finger F to provide additional support.

In various tested embodiments of the invention, the splints 10, 30 and 50 and the splint extension 20 were of sheet aluminum. It will be appreciated that other flexible metallic and non-metallic materials which are able to hold a prescribed contour as a result of bending may also be employed.

Moreover, while various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. A splint for providing lateral and vertical support to an injured member comprising a base strip having an edge bounding opposed surfaces and being bendable into a desired configuration according to the support required for said member; and a plurality of individual projections having base portions positioned at the end of said base strip and extending upwardly therefrom;

each projection being separated at its base portion from an adjoining projection by a gap which extends to a groove on the outer surface of said base strip;

thereby to facilitate the shaping of said base strip and its reduction to a desired size.

2. Apparatus as defined in claim 1 wherein said projections are disposed at a right angle with respect to said base strip.

* * * * *